United States Patent [19]

Singh

[11] Patent Number: 5,512,249
[45] Date of Patent: Apr. 30, 1996

[54] STERILIZING APPARATUS

[75] Inventor: Vijay Singh, Bernardsville, N.J.

[73] Assignee: Schering Corporation, Kenilworth, N.J.

[21] Appl. No.: 336,898

[22] Filed: Nov. 10, 1994

[51] Int. Cl.$^6$ .................................................. F16K 31/00
[52] U.S. Cl. ........................ 422/114; 137/241; 137/468; 422/107; 422/115; 422/116; 422/119; 422/292
[58] Field of Search ..................... 422/114, 115, 422/107, 116, 119, 292, 108, 109, 905; 137/468, 241; 251/335.2; 236/93 R; 222/54

[56] References Cited

U.S. PATENT DOCUMENTS

| | | | |
|---|---|---|---|
| 2,593,129 | 4/1952 | Fischer | 137/468 |
| 2,638,920 | 5/1953 | Woodhull | 137/468 |
| 4,261,382 | 4/1981 | Bridges | 137/187 |
| 4,336,821 | 6/1982 | Frantz et al. | 137/187 |
| 4,505,427 | 3/1985 | Bridges | 236/54 |
| 4,612,872 | 9/1986 | Whelchel et al. | 137/468 X |
| 4,635,668 | 1/1987 | Netter | 137/62 |
| 4,653,526 | 3/1987 | Hoiss | 137/241 X |
| 4,745,964 | 5/1988 | Mower et al. | 165/40 |
| 4,746,223 | 5/1988 | Miyata et al. | 374/103 |
| 4,971,764 | 11/1990 | Albright | 422/110 |
| 4,989,649 | 2/1991 | Weiler et al. | 137/241 X |
| 5,026,524 | 6/1991 | Powell et al. | 422/108 X |
| 5,063,956 | 11/1991 | Borcuch et al. | 137/14 |
| 5,287,876 | 2/1994 | Takahashi | 137/468 X |

OTHER PUBLICATIONS

Pyco Resistance Thermometers, Sales Literature Pyco, Inc. Penndel, PA. Publication date unknown.
Sanitary Diaphragm Valves, Sales Literature Published by Gemu, Apr., 1992.
CN132 Autotone Temperature Controller, Operators Manual—Omega Technology Company 1993.

*Primary Examiner*—Jill Warden
*Assistant Examiner*—Krisanne M. Thornton
*Attorney, Agent, or Firm*—Warrick E. Lee, Jr.

[57] ABSTRACT

Apparatus for sterilizing a transfer conduit having (a) a source of steam connected to the transfer conduit, (b) a condensate conduit for draining steam condensate from the transfer conduit, (c) a valve in the condensate conduit having a valve body with an upstream portion and a downstream portion, the portions are separated by a rapidly opening flow control means, such as a diaphragm, (d) a temperature sensor in the upstream portion of the valve body, and (e) a temperature controller connected to the temperature sensor adapted to read the temperature in the upstream portion of the valve body and to open the valve when the temperature drops below a fixed set point and to close the valve when the temperature is above the fixed set point.

A steam condensate drain control system and a steam condensate valve are also described and claimed.

11 Claims, 2 Drawing Sheets

STERILIZING APPARATUS

BACKGROUND OF THE INVENTION

This invention pertains to sterilizing apparatus, and particularly to apparatus for sterilizing with steam and efficiently draining steam condensate from the apparatus. This invention is especially suitable for sterilizing fluid transfer conduits, such as those used in the pharmaceutical and biotech industries.

Typical prior art methods for draining condensate from steam sterilizing systems use steam traps. However steam traps have small, winding flow passages that are easily clogged. Once a steam trap is clogged, the apparatus to be sterilized will not be subjected to a sufficiently high temperature for a sufficiently long time to achieve sterilization. Government regulations, such as those of the Food and Drug Administration, typically require that items to be sterilized be subjected to a temperature of at least 120.5° C. for about 60 minutes.

U.S. Pat. Nos. 4,261,382 and 4,505,427 (both to Bridges) relate to condensate drainage systems wherein a controlled valve is used instead of a steam trap. The temperature is measured by a sensor in the condensate drainage conduit. A temperature controller positions the valve, opening it when the temperature is too low and closing it when the temperature is too high. The trouble with the Bridges systems is that the portion of the conduit between the temperature sensor and the valve will always be filled with condensate that is below the sterilization temperature, thereby making it likely that portions of the equipment being sterilized will not be subjected to the full sterilizing temperature during the entire sterilization time.

The present invention overcomes this problem by locating the temperature sensor in the valve body, upstream of the valve closure, e.g. a diaphragm.

U.S. Pat. No. 4,336,821 (Frantz et al.) relates to a valve for draining liquid from a compressed gas reservoir having a sensor in the valve body. However, this sensor detects build up of liquid. The temperature in the valve body has nothing to do with whether the valve will open of close. Frantz et al. do disclose a temperature control device, but its purpose is to turn on a heater when the ambient temperature drops below a fixed point to prevent the valve from freezing. The flow of steam condensate is not regulated in response to system temperature.

SUMMARY OF THE INVENTION

The present invention comprises apparatus for sterilizing a transfer conduit comprising:

(a) a source of steam connected to said transfer conduit (b) a condensate conduit for draining steam condensate from said transfer conduit, (c) a valve in said condensate conduit comprising a valve body having an upstream portion and a downstream portion, said portions separated by a rapidly opening flow control means, (d) a temperature sensor in said upstream portion of said valve body, (e) a temperature controller connected to said temperature sensor adapted to read the temperature in the upstream portion of the valve body and to open said valve when the temperature drops below a fixed set point and to close said valve when the temperature is above the fixed set point.

A preferred valve for this invention is a diaphragm valve. It is preferred that the temperature sensor send an electrical signal to the temperature controller and that the controller opens and closes the valve by sending an electrical signal to a solenoid located on the valve. A preferred controller has an adjustable gain and cycle time, means for computing the difference between the temperature sensed in the upstream portion of the valve and the set point temperature, means for multiplying that difference by the gain to obtain an "on time", wherein the controller opens the valve for a period equal to the "on time" and during the remainder of the cycle time the valve is closed.

Another aspect of this invention comprises a steam condensate drain system comprising the valve and temperature control system described above. Yet another aspect of this invention is a steam condensate control valve.

DETAILED DESCRIPTION OF THE INVENTION

Figure 1:
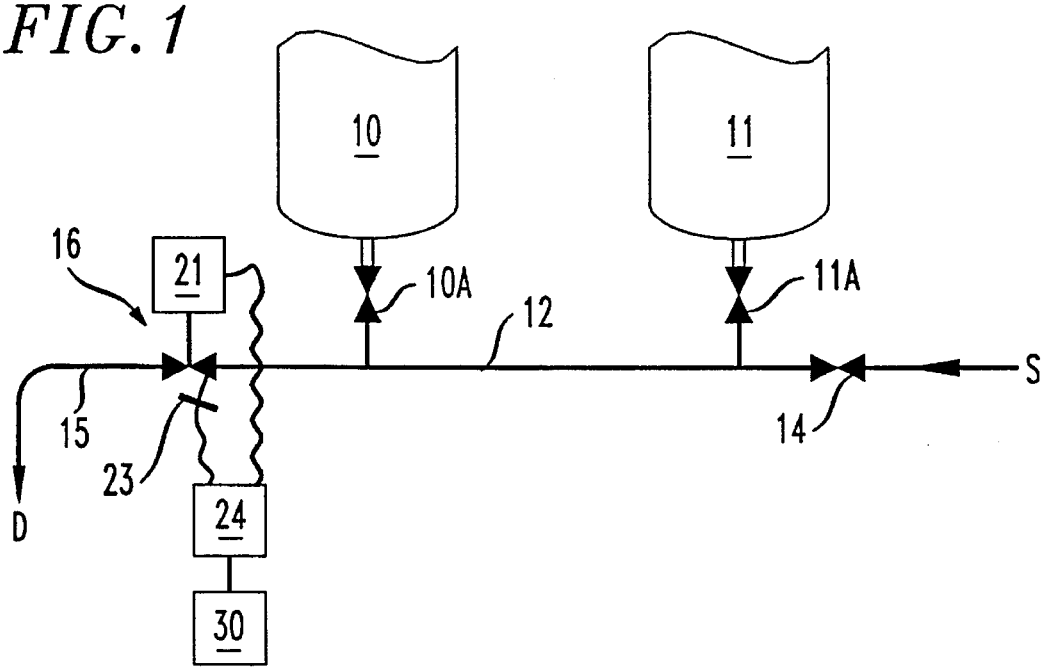
FIG. 1 is a schematic illustration of conduit sterilizing apparatus in accordance with the invention.

Referring to FIG. 1, assume it is desired to transfer fluid from vessel 10 through transfer valve 10A to vessel 11 (via transfer valve 11A) under sterile conditions through transfer conduit 12. To accomplish the sterile transfer, conduit 12 must first be sterilized by steam which enters the conduit from steam source S connected to conduit 12. Valve 14 is used to regulate the flow of steam into conduit 12. Steam condensate may be drained from transfer conduit 12 via condensate conduit 15 to drain D. Instead of the usual steam trap common for prior-art systems, a special valve 16 is installed in condensate conduit 15.

Figure 2:
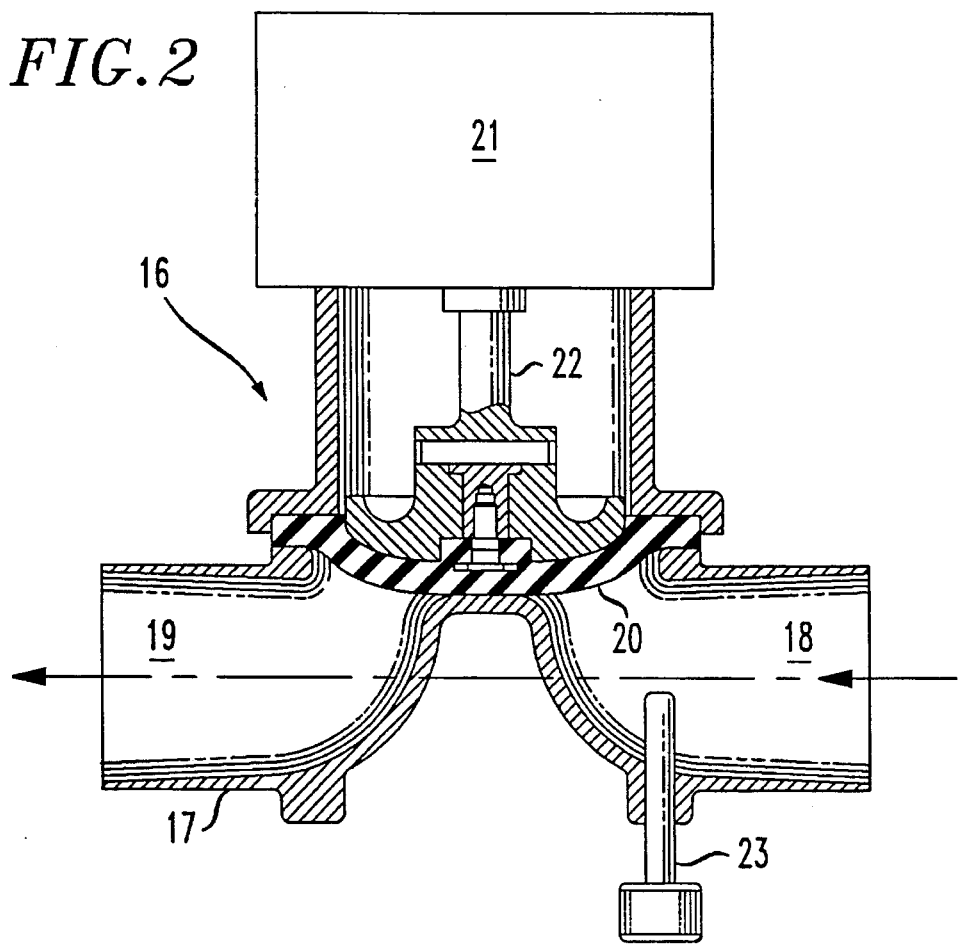
FIG. 2 illustrates a preferred valve that may be used as part of the inventive apparatus. This view is partially in section, as indicated by the cross hatching

As illustrated in FIG. 2 valve 16 has a valve body 17 having an upstream portion 18 and a downstream portion 19. The terms "upstream" and "downstream" are intended to have their usual meaning. If fluid is flowing through valve body 17 in the direction of the arrows, the first portion of the valve body that encounters the flowing fluid (18 in this case) is the upstream portion and the last portion to encounter the fluid is the downstream portion (19 in this case). The upstream and downstream portions of the valve body are separated by a rapidly opening flow control means, which is capable of rapidly starting and stopping the flow of fluid through the valve body. The preferred flow control means is a solenoid-operated diaphragm 20, which, in the closed position, is pushed against a portion of the valve body to prevent flow of fluid through the valve body. The position of diaphragm 20 is controlled by solenoid 21 which moves stem 22 up and down (when the valve is oriented as shown in FIG. 2) to move the diaphragm from the closed to the open position and vice versa. Of course other types of quick opening valves could be used with the invention such as ball and gate valves. In that case the rapidly opening flow control means would be the ball or gate connected to an actuation device, such as a solenoid. The preferred valve to use with this invention is a TYPE 605 solenoid-operated diaphragm valve available from the GEMU Company, Ingelfingen, Germany.

A temperature sensor 23 is installed in upstream portion 18 of valve body 17. Preferably the temperature sensor is a simple thermocouple, which is well known in the art of temperature control. The thermocouple produces an electrical signal, the voltage of which varies in proportion to the temperature experienced by the thermocouple. The most preferred temperature sensor is a PYCO model RTD, available from Omega Technologies Company, Stamford, Connecticut.

Returning now to FIG. 1, a temperature controller 24 is connected to temperature sensor 23. Temperature controller 24 is adapted to read the temperature in the upstream portion of the valve body, as sensed by temperature sensor 23, and to open valve 16 when the temperature drops below a fixed set point Temperature controller 24 is also adapted to close valve 16 when the temperature is above the set point. Temperature controller 24 may be any of the well known automatic temperature controllers that have been used throughout the chemical and pharmaceutical industries for many years.

It is preferable to use an electrical/electronic temperature control system wherein temperature sensor 23 sends an electrical signal to temperature controller 24 and the controller opens valve 16 by sending an electrical signal to solenoid 21 adapted to open and close valve 16.

It is most preferable for the controller to have an adjustable gain and cycle time. Ideally when the temperature is below the set point, the controller calculates the difference between the set point temperature and the actual temperature and multiplies the difference (or error) by the gain to obtain an "on time" during which the controller causes valve 16 to open. The "on time" constitutes a portion of the cycle time. During the remainder of the cycle time, the valve is closed. By experimenting with the cycle time and gain, it is possible to fine tune the system so that excellent temperature control is achieved with minimal steam consumption. The preferred controller for this invention is an OMEGA model CN132 Autotune Temperature Controller available from Omega Technologies Company Stamford, Conn. When the preferred temperature controller, valve and temperature sensor are used, it has been found that optimal results for sterilizing a 1 inch (2.5 cm) diameter transfer conduit having a length of 10 feet (3 meters) are obtained if the cycle time is set at 5 to 60 seconds, more preferable about 5 seconds and the gain is set in the range of from 10% to 100%, more preferable about 30%.

An optional feature for use with this invention is a data logging system 30 connected to controller 24. When this feature is used, the temperature sensed by sensor 23 is retransmitted to data logging system 30, which records the sensed temperature while sterilization is taking place. In its simplest form data logging system 30 may be a temperature recorder. The recorded temperature can be used verify and validate that the proper temperature was reached and maintained in the transfer line for the required time.

The apparatus illustrated in FIGS. 1 and 2 functions as follows. With transfer valves 10A and 11A closed, steam valve 14 is opened and temperature controller 24 is set to control the temperature to the desired sterilization temperature. This causes controlled valve 16 to pulse between its open and closed positions to maintain transfer conduit 12 at the desired sterilizing temperature, typically 120.5 °C. This action is continued for the desired sterilization time, after which transfer conduit 12 will be sterile. Steam valve 14 is then closed and temperature controller 24 is deactivated, causing valve 16 to close. Transfer valves 10A and 11A are then opened and material is transferred from vessel 10 to vessel 11, usually by pressurizing vessel 10. After the transfer, transfer valves 10A and 11A are closed and transfer conduit 12 may be sterilized again by the same procedure.

In addition to achieving better temperature control with less maintenance, the apparatus of the present invention has another advantage over conventional condensate drainage systems using steam traps. The inventive apparatus can act as a drain valve for the transfer vessels.

Figure 3:
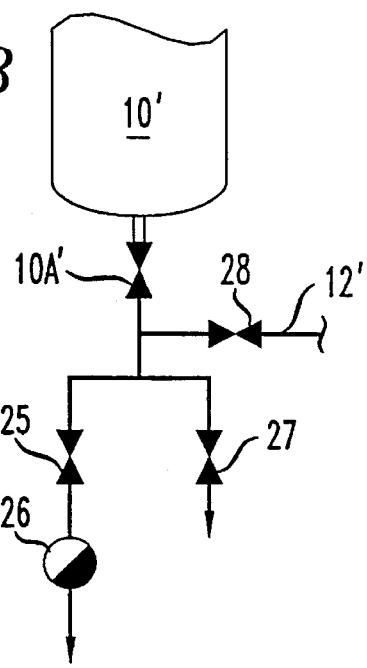
FIG. 3 is a schematic illustration of prior-art sterilizing apparatus.

FIG. 3 show a conventional condensate drainage system using a steam trap 26. To drain the contents of vessel 10', valve 28 is closed to prevent the material from flowing into transfer conduit 12'. Next valve 25 is closed to prevent the material from flowing into steam trap 26. Finally valves 10A' and 27 are opened and the material from vessel 10 is drained through valves 10A' and 27 and their associated conduits as shown in FIG. 3. Of course during the draining the steam valve to conduit 12', not shown, is closed.

Figure 4:
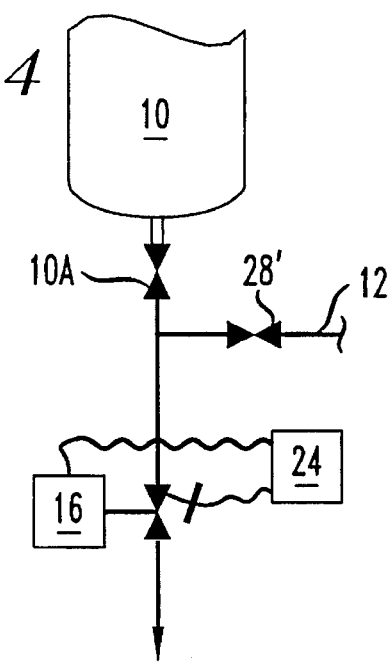
FIG. 4 is a schematic illustration of conduit sterilizing apparatus in accordance with this invention, showing how the apparatus may be used as a system drain.

FIG. 4 illustrates how the apparatus of the present invention may be used to drain vessel 10. Valve 28' is closed to prevent the material from flowing into transfer conduit 12. The steam valve to conduit 12, not shown, is kept closed. Temperature controller 24 is activated and transfer valve 10A is opened. Since the temperature control system associated with controller 24, described previously, will encounter only cool material, well below the sterilization temperature, valve 16 will fully open and drain the material from vessel 10. Comparing FIGS. 3 and 4, it is immediately evident that the system of the present invention, FIG. 4, requires two less valves (25 and 27) than the prior art system of FIG. 3. Of course the piping associated with valves 25 and 27 is also not required by the present system.

Figure 5:
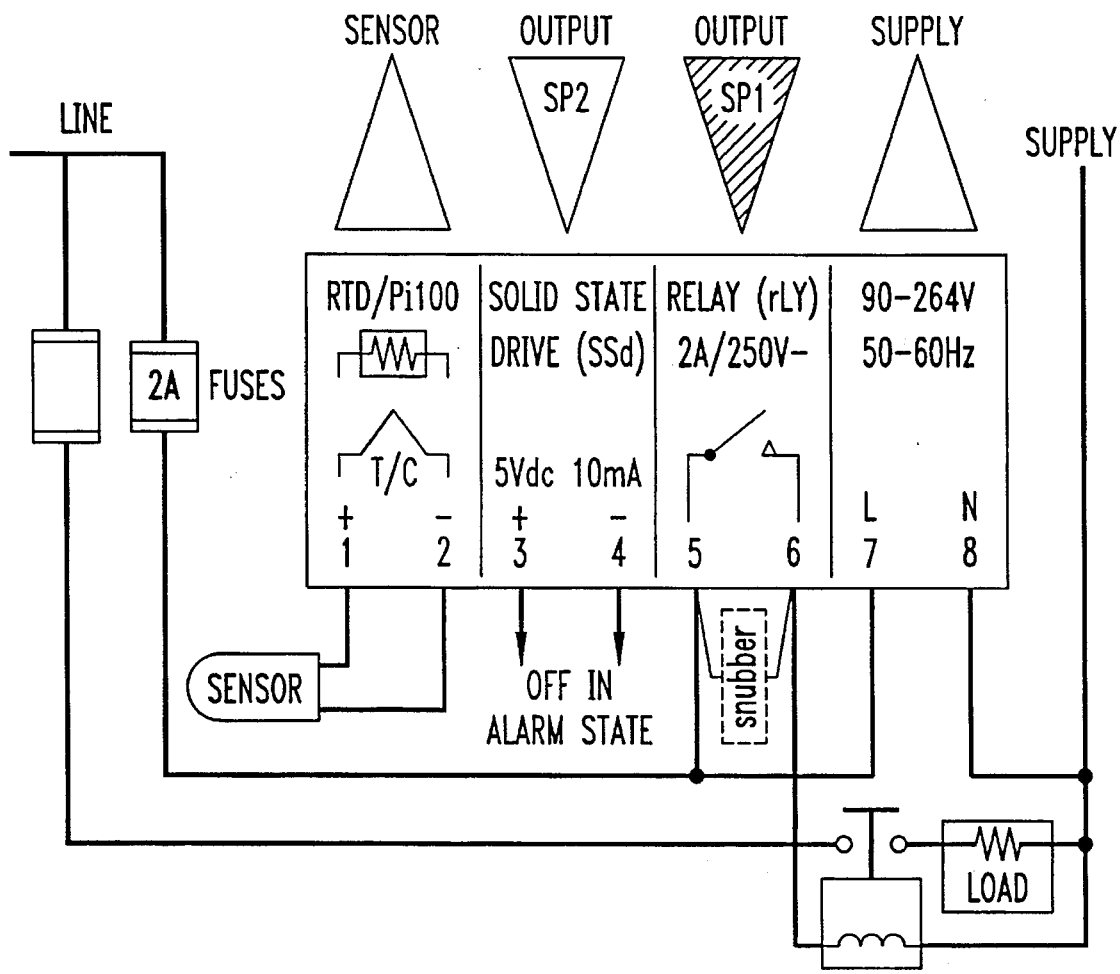
FIG. 5 is a schematic illustration of a preferred control circuit for use with this invention.

FIG. 5 illustrates a preferred control circuit for temperature controller 24, which functions as follows. The temperature signal is read from the sensor inputs. If the temperature is below the setpoint, the temperature controller activates the output relay. This relay in turn opens the condensate valve. As steam flows through the valve, the temperature sensed by the controller rises. When the preset cycle time elapses, the valve closes. The fraction of the cycle time that the valve remains open is proportional to the difference between the measured temperature and the setpoint (Gain). If on completion of a cycle the temperature is still below the setpoint, the cycle is repeated, otherwise, the valve remains shut until the temperature drops below the setpoint.

It is clear from the above description that the apparatus of the present invention provides a sterilization system with much better assurance that the required temperature will be maintained for the full sterilization time than prior art systems. Furthermore the inventive system requires less maintenance than conventional steam trap systems. The inventive apparatus can provide vessel drainage without requiring the additional valves and piping required by conventional steam trap systems.

I claim:

1. Apparatus for sterilizing a transfer conduit comprising:

(a) a transfer conduit to be sterilized, (b) a source of steam connected to said transfer conduit, (c) a condensate conduit for draining steam condensate from said transfer conduit, (d) a valve in said condensate conduit comprising a valve body having an upstream portion and a downstream portion, said portions separated by a flow control means selected from the group consisting of diaphragm, a ball, and a gate, (e) a temperature sensor constructed and arranged to sense the temperature in said upstream portion of said valve body, (f) a temperature controller connected to said temperature sensor constructed and arranged to read the temperature sensed by said temperature sensor in the upstream portion of the valve body and to open said valve when the temperature drops below a fixed set point and to close said valve when the temperature is above the fixed set point.

2. The sterilizing apparatus of claim 1 wherein said valve is a diaphragm valve.

3. The sterilizing apparatus of claim 2 wherein said temperature sensor is constructed and arranged to send an electrical signal to said temperature controller and said controller is constructed and arranged to open and close said valve by sending an electrical signal to a solenoid located on said valve.

4. The sterilizing apparatus of claim 3 wherein said controller has an adjustable gain and cycle time, means for computing the difference between the temperature sensed in the upstream portion of the valve and the set point temperature, means for multiplying that difference by the gain to obtain an "on time", wherein the controller opens the valve for a period equal to the "on time" and during the remainder of the cycle time the valve is closed.

5. The apparatus of claim 1 further comprising a temperature recorder connected to said temperature controller for recording the temperature sensed by said sensor over a period of time.

6. A steam condensate drain control system comprising:

(a) a valve body having an upstream portion connected to a source of steam and steam condensate and a downstream portion, said portions separated by a flow control means selected from the group consisting of a diaphragm, a ball, and a gate, (b) a temperature sensor constructed and arranged to sense the temperature in said upstream portion of said valve body, (c) a temperature controller connected to said temperature sensor constructed and arranged to read the temperature sensed by the temperature sensor in the upstream portion of the valve body and to open said valve when the temperature drops below a fixed set point and to close said valve when the temperature is above the fixed set point.

7. The condensate drain control system of claim 6 wherein said valve is a diaphragm valve.

8. The condensate drain control system of claim 7 wherein said temperature sensor is constructed and arranged to send an electrical signal to said temperature controller and said controller is constructed and arranged to open and close said valve by sending an electrical signal to a solenoid located on said valve.

9. The condensate drain control system of claim 8 wherein said controller has an adjustable gain and cycle time, means for computing the difference between the temperature sensed in the upstream portion of the valve and the set point temperature, means for multiplying that difference by the gain to obtain an "on time", wherein the controller opens the valve for a period equal to the "on time" and during the remainder of the cycle time the valve is closed.

10. A steam condensate control valve comprising:

(a) a valve body having an upstream portion connected to a source of steam and steam condensate and a downstream portion, said portions separated by a flow control means selected from the group consisting of a diaphragm, a ball, and a gate, (b) a temperature sensor constructed and arranged to sense the temperature in said upstream portion of said valve body, and (c) means for actuating said flow control means.

11. The steam condensate control valve of claim 10 wherein said element (c) actuating means is a solenoid.

* * * * *